United States Patent
Wustenberg et al.

(10) Patent No.: US 9,248,097 B2
(45) Date of Patent: *Feb. 2, 2016

(54) MUCOSOMAL ALLERGEN-SPECIFIC IMMUNOTHERAPY WITH INITIAL DOSING AFTER START OF POLLEN SEASON

(75) Inventors: Eike Gunther Wustenberg, Hamburg (DE); Eckhard-Carl Albrecht Puchert, Hamburg (DE)

(73) Assignee: ALK-ABELLO A/S, Horsholm (DK)

( * ) Notice: Subject to any disclaimer, the term of this patent is extended or adjusted under 35 U.S.C. 154(b) by 12 days.

This patent is subject to a terminal disclaimer.

(21) Appl. No.: 12/988,513

(22) PCT Filed: Apr. 8, 2009

(86) PCT No.: PCT/EP2009/054186
§ 371 (c)(1),
(2), (4) Date: Mar. 1, 2011

(87) PCT Pub. No.: WO2009/124954
PCT Pub. Date: Oct. 15, 2009

(65) Prior Publication Data
US 2011/0142934 A1    Jun. 16, 2011

Related U.S. Application Data

(60) Provisional application No. 61/044,401, filed on Apr. 11, 2008.

(30) Foreign Application Priority Data

Apr. 11, 2008    (DK) .................. 2008 00533

(51) Int. Cl.
*A61K 38/00* (2006.01)
*A61K 39/00* (2006.01)
*A61K 39/35* (2006.01)
*A61K 39/36* (2006.01)
*A61K 39/38* (2006.01)
*A61K 9/00* (2006.01)

(52) U.S. Cl.
CPC .............. *A61K 9/006* (2013.01); *A61K 39/35* (2013.01); *A61K 9/0056* (2013.01); *A61K 2039/542* (2013.01); *A61K 2039/545* (2013.01)

(58) Field of Classification Search
None
See application file for complete search history.

(56) References Cited

U.S. PATENT DOCUMENTS

2005/0175638 A1    8/2005    Esch
2006/0115499 A1    6/2006    Brimnes et al.

FOREIGN PATENT DOCUMENTS

| CN | 101065146 B | 11/2012 | |
|---|---|---|---|
| DE | 202007004567 U1 | 10/2007 | |
| WO | WO 94/11734 A1 | 5/1994 | |
| WO | WO 99/57542 A2 | 12/1999 | |
| WO | WO 2004/047793 * | 6/2004 | ............ A61K 39/35 |
| WO | WO 2004/047794 A2 | 8/2004 | |
| WO | WO-2005/077410 A1 | 8/2005 | |
| WO | WO-200583385 A2 | 9/2005 | |
| WO | WO 2006/050729 A2 | 5/2006 | |
| WO | WO-2006/050729 A2 | 5/2006 | |
| WO | WO-2007051476 A1 | 5/2007 | |
| WO | WO 2008/116936 * | 10/2008 | ............ A61K 39/35 |

OTHER PUBLICATIONS

Lee, Lyna K. et al., "Agressive coseasonal immunotherapy in mountain cedar pollen allergy," Arch Otoiaryngol, vol. 108, Dec. 1982, pp. 787-794.

Dahl, Ronald et al., Sublingual grass allergen tablet immunotherapy provides sustained clinical benefit with progressive immunolic changes over 2 years, Journal of Allergy Clin. Immunol, Feb. 2008, pp. 512-518 vol. 121, No. 2.

Frati, Franco et al., Mucosal immunization application to allergic disease: Sublingual immunotherapy, Allergy and Asthma Proceedings, Jan.-Feb. 2007, pp. 35-39, vol. 28, No. 1.

Frew, Anthony J. et al., Efficacy and safety of specific immunotherapy with SQ allergen extract in treatment-resistant seasonal allergic rhinoconjunctivitis, Journal of Allergy Clin. Immunol, Feb. 2006, pp. 319-325, vol. 117, No. 2.

Kleine-Tebbe, J. et al., Safety of a SQ-standardised grass allergen tablet for sublingual immunotherapy: a randomized, placebo-controlled trial, Allergy, 2006, pp. 181-184, vol. 61.

Kopp, Matthias V. et al., Applikationsformen der spezifischen Immuntherapie, Allegro J., 2007, pp. 570-575, vol. 16.

Niggemann, B. et al., Five-year follow-up on the PAT study: specific immunotherapy and long-term prevention of asthma in children, Allergy, 2006, p. 855-859, vol. 61.

Novembre, Elio et al., Coseasonal sublingual immunotherapy reduces the development of asthma in children with allergic rhinoconjunctivitis, Journal of Allergy Clin. Immunol, Oct. 2004, pp. 851-857, vol. 114, No. 4.

Ott, H. et al., ECRIT-study: efficacy and safety of coseasonal SLIT in patients with grass pollen allergy over a 3 year period, Allergy, 2007, vol. 62 (Suppl. 83), Article 176, p. 72.

Seindenberg, J. et al., Evaluation of the safety of a seasonal ultra rush high-does sublingual immunotherapy in children with allergic rhinitis to tree pollen and grass pollen, Clinical and Experimental Allergy, 2006, vol. 36, No. 9.

Kuby et al., Immunology, Fourth Edition, Chapter 18, pp. 449-465, Jan. 15, 2000.

(Continued)

*Primary Examiner* — Nora Rooney
(74) *Attorney, Agent, or Firm* — Birch, Stewart, Kolasch & Birch, LLP

(57) ABSTRACT

The present invention relates to mucosal allergen-specific immunotherapy with a seasonal allergen, wherein the therapy is initiated after start of the pollen season of the seasonal allergen. Preferably, the seasonal allergen is provided in solid dosage form and is administered daily. Furthermore, advantageously, the same dose may be used throughout the treatment period since up-dosing is not required.

25 Claims, No Drawings

(56) References Cited

OTHER PUBLICATIONS

Sledge, Robert F., "Treatment of hay fever with alum-precipitated pollen extract," U.S. Nav. Med. Bull., 1938, vol. 36, pp. 18-29.

Roy Patterson, MD et al., "Rush immunotherapy in a dog with severe ragweed and grass pollen allergy," Annals of Allergy, Asthma, & Immunology, Sep. 1999, vol. 83, pp. 213-216.

Freeman, J., "Further observations on the treatment of hay fever by hypodermic inoculations of pollen vaccine," The Lancet, Sep. 16, 2011, pp. 814-817.

Vervloet, D. et al., "Safety and Efficacy of *Juniperus ashei* Sublingual-Swallow Ultra-Rush Pollen Immunotherapy in Cypress Rhinoconjunctivitis," Int Arch Allergy Immunol, vol. 142, pp. 239-246, 2007.

Alvarez-Cuesta, E. et al., "Standards for practical allergen-specific immunotherapy," Allergy, vol. 61, Suppl. 82, pp. 1-20, 2006.

Bowen, T. et al., "Canadian trial of sublingual swallow immunotherapy for ragweed rhinoconjunctivitis," Ann Allergy Asthma Immunol., vol. 93, pp. 425-430, 2004.

Calderon, M.A. et al., "Prolonged preseasonal treatment phase with Grazax sublingual immunotherapy increases clinical efficacy," Allergy, vol. 62, pp. 958-961, 2007.

Lombardi, C. et al., "Adminitration regimens for sublingual immunotherapy to pollen allergens: What do we know?" Allergy, vol. 64, pp. 849-854, 2009.

Reich, K. et al., "Immunologic Effects and Tolerability Profile of In-Season Initiation of a Standardized-Quality Grass Allergy Immunotherapy Tablet: A Phase III, Multicenter, Randomized, Double-Blind, Placebo-Controlled Trial in Adults with Grass Pollen-Induced Rhinoconjunctivitis," Clinical Therapeutics, vol. 33, No. 7, pp. 828-840, 2011.

Bousquet, J. et al., "Allergen immunotherapy: therapeutic vaccines for allergic diseases," WHO Position Paper, pp. 1-42, Jan. 1997.

Content of Edition "Allergologia at Immunopathologia", vol. (Madr.) 36, No. 2, Mar. 2008.

Dahl at al., "Efficacy and safety of sublingual immunotherapy with grass allergen tablets for . . . ", Journal of Allergy and Clinical Immunology, 2006; 118: 434-440.

Dahl at al., "Specific immunotherapy with SQ standardized grass allergen tablets in asthmatics with rhinoconjunctivitis", Allergy, 2006: 61:185-190.

D'Anneo et al., "Parletaria sublingual allergoid immunotherapy with a co-seasonal treatment schedule", Allergol. Immunopathol. (Madr.) 36:79-84, (2008).

Durham et al., "Sublingual Immunotherapy with once-daily grass allergen tablets . . . ", Journal of Allergy and Clinical Immunology, 2006; 117: 802-809.

Janeway et al., "The Immune System in Health and Disease", Figure 4.1.6 on p. 143 of Immunobiology, 5th edition, 2001.

Letter of the Patentee to the EPO dated Aug. 5, 2011.

Malting et al., "Safety and Immunological Changes During Sublingual Immunotherapy . . . ", J. Investig Allergol Clin Immunol, 2006; 16(3): 162-168.

Moreno-Ancillo at al., "Efficacy and Quality of Life With Once-Daily Sublingual Immunotherapy . . . ", J Investig Allergoi Clin Immunol, 2007; 17(6): 399-405.

Passalacqua et al., "The Safety of Allergen Specific Sublingual Immunotherapy", Current Drug Safety 2 (2007) 117-123.

Press Release "ALK-AbellO Announces Positive Results from Grass Tablet Study", (2005).

Rodriguez at al., "Once Daily Sublingual Immunotherapy without Updosing—A New Treatment Schedule", Int Arch Allergy Immunol, 2006; 140: 321-326.

University of Birmingham (Jan. 2006) "Grazax allergy vaccine for moderate to severe seasonal allergic rhintis".

Wustenberg et al., "Restrospective analysis of the tolerability of initiating the ALK grass allergen tablet . . . ", Allergy, 2008; 63 (Suppl. 88): 637-638..

* cited by examiner

MUCOSOMAL ALLERGEN-SPECIFIC IMMUNOTHERAPY WITH INITIAL DOSING AFTER START OF POLLEN SEASON

This Application is the National Phase Under 35 U.S.C. §371 of PCT International Patent Application No. PCT/EP2009/054186 which has an International filing date of Apr. 8, 2009, which claims priority to both U.S. Provisional Patent Application No. 61/044,401 filed on Apr. 11, 2008 and Danish Patent Application No. PA 2008 00533 filed on Apr. 11, 2008. The entire contents of all applications listed above are hereby incorporated by reference.

TECHNICAL FIELD

The present invention relates to allergen-specific immunotherapy with mucosomal administration of allergen for preventing or treating allergy caused by seasonal allergens.

BACKGROUND

Currently, the treatment of allergic disease is based on allergen avoidance, pharmacotherapy for symptom relief, and allergen-specific immunotherapy (SIT). SIT is the only treatment modality with the potential of altering the natural course of the disease by increasing immunological tolerance, thereby entailing sustained reductions in symptoms.

Subcutaneous allergen injections have been the main approach for conducting SIT, which include weekly to monthly subcutaneous injections to allergic patients with a selected allergen over an extended period of time (SCIT immunotherapy)

However, recently another route of administering the allergen has been proven effective, namely sublingual administration, which offers several advantages compared with the subcutaneous route, including increased convenience, compliance, and safety. For example, the risk of severe systemic allergic reactions following sublingual allergen-specific immunotherapy is considered as being low as the oromucosal administration of allergens does not lead to absorption into the vascular system to any significant extent. However, other mild to moderate side reactions are still seen in some patients, e.g. in the form of local allergic reactions, oral itching and sublingual oedema. Sublingual allergen-specific immunotherapy (SLIT) is today carried out by administering the allergen in liquid dosage form (droplets or spray) or in solid dosage form (tablet).

For reasons of safety, specific-allergen-specific immunotherapy has conventionally been performed with a dosing regimen that is divided in two consecutively treatment phases, namely an up-dosing phase where increasing doses are administered until an effective and safe treatment dose has been reached, which dose is used throughout the maintenance phase. Typically, the up-dosing phase in SCIT comprises weekly injections over a 4 months period and the maintenance phase comprises monthly injections. With SLIT, the up-dosing phase may be conducted over a shorter period and doses are administered more frequently.

Current knowledge suggests that success of allergen-specific immunotherapy depends on the cumulative dose of allergen administered (*Kopp and Heinzmann, Applikationsformen der spezifiscien Immuntherapie, Allergo J* 16, 570-5, 2007). Therefore, faster up-dosing phases, such as over a 5 days-period (Rush up-dosing phase) or over even fewer days (Ultra-Rush up-dosing phase) with higher doses of allergen have been applied in some circumstances. Up-dosing is also applied with sublingual administration of allergen in liquid dosage form (table 2 in *Kopp and Heinzmann* 2007).

With respect to allergen-specific immunotherapy with seasonal allergens, such as allergens derived from pollen, there is an additional precaution to make in conducting SIT. Currently, to avoid an exaggerated allergen load it is required to start the allergen-specific immunotherapy at least 2-4 months prior to the pollen season. This requirement of initiating immunotherapy prior to the pollen season is based on the fact that during the pollen season the immune system of an allergic subject is already "primed" by pollen in the air and this may lead to the occurrence of more adverse events related to treatment when treatment is initiated during this period. For example, in current approved SLIT, the sublingual administration of the allergen in tablet formulation comprises no up-dosing phase, but the immunotherapy has to be initiated 4 months before the pollen season (table 2 in *Kopp and Heinzmann* 2007).

However, many subjects have their first visit to the physician concerning their allergic complaints when they experience the symptoms, i.e. during the pollen season, and today, these subjects can only be offered symptomatic therapy. Usually, subjects are told to return after the pollen season to start immunotherapy, but this rarely happens because they forget the appointment once they do not experience the symptoms anymore. Presently, these subjects can only be offered symptomatic therapy based on the recommendation described above.

Therefore, there is still a need for improved allergen-specific immunotherapy, where more patients can benefit to safe and effective treatment.

Seidenberg et al. (*Clinical and Experimental Allergy*, 36, 1201-1212, *British Society for Allergy and Clinical Immunology, Annual Conference—July* 2006, *Abstract S*17) describes immunotherapy treatment of children with a liquid allergy vaccine comprising a seasonal allergen that is administered sublingually and includes an up-dosing phase that is initiated shortly before the start of the season or during the season.

DE Utility Model 20 2007 004 567.0 discloses allergen-specific immunotherapy with seasonal allergen by parenteral administration, wherein the dosage regimen comprises an up-dosing phase that is initiated after start of the pollen season.

WO 2007/051476 discloses the use of an allergen for the manufacture of a liquid vaccine formulation for preventing or treating allergy in a subject by oromucosal administration in a dosage regimen comprising no up-dosing.

Ronald Dahl et al (in sublingual grass allergen-specific immunotherapy provides sustained clinical benefit with progressive immunologic changes over 2 years, *J Allergy Clin Immunol* vol 121, No 2, p 512-518, 2007) discloses allergen-specific immunotherapy with a solid dosage form comprising a seasonal allergen that is administered sublingually in a daily dosing regimen where immunotherapy was initiated 4-8 months before the anticipated start of the grass pollen season and treatment was continued after end of the grass pollen season.

SUMMARY OF INVENTION

The present inventors have proven that, unlike the expectation of having a higher risk of experiencing adverse events, allergen-specific immunotherapy comprising administering a seasonal allergen by mucosal administration for treatment of allergy to seasonal allergens is equally well-tolerated and effective too when started intra-seasonally as when started pre-seasonally.

This finding is very surprising in the sense that it has hitherto been recommended and in fact required practice that for seasonal allergens it is necessary to start mucosal allergen-specific immunotherapy, well in advance of the season to reduce side effects and in particularly to avoid the risk of severe side effects, such as anaphylactic shock. Advantageously, the intra-seasonal start of immunotherapy could be performed without using up-dosing phase and still serious adverse events were not observed. Thus, the dosage regimen does not comprise separate up-dosing phase and maintenance phase, but the same treatment dose (mono-dose) was administered throughout the treatment period.

Accordingly, a first aspect of the invention relates to a solid dosage form suitable formulated for mucosal administration comprising a seasonal allergen composition for use in allergen-specific immunotherapy for preventing or treating allergy to said allergen composition in a subject by mucosal administration, the solid dosage form is administered in a dosage regimen, wherein initial administration to said subject is performed within the allergen season of the allergen composition. As a further advantage, the allergen-specific immunotherapy may be performed in a dosage regimen that is a mono-dose regimen, i.e. wherein only one dose of allergen composition is used throughout the entire treatment period. In other words, the dosing regimen comprises no up-dosing phase, i.e. the initial administration is performed without up-dosing phase.

Alternatively worded, a first aspect relates to a method of doing allergen-specific immunotherapy for preventing or treating allergy to a seasonal allergen composition, comprising administering by mucosal administration to a subject in need thereof a solid dosage form containing a seasonal allergen, the solid dosage form is administered in a dosage regimen, wherein initial administration to said subject is performed within the allergen season of the allergen composition.

Furthermore, alternatively to perform the immunotherapy with administering the allergen in solid dosage form, another aspect of the invention relates to a liquid dosage form suitable formulated for mucosal administration comprising a seasonal allergen composition for use in allergen-specific immunotherapy for preventing or treating allergy to said allergen composition in a subject by mucosal administration, the liquid dosage form is administered in a dosage regimen, wherein initial administration to said subject is performed within the allergen season of the allergen composition and without up-dosing phase.

Alternatively worded, another aspect relates to a method of doing allergen-specific immunotherapy for preventing or treating allergy to a seasonal allergen composition, comprising administering by mucosal administration a liquid dosage form containing the seasonal allergen to a subject in need thereof, the solid dosage form is administered in a dosage regimen, wherein initial administration to said subject is performed within the allergen season of the allergen composition and without up-dosing phase.

DETAILED DESCRIPTION

In connection with the present invention the following definitions are used:

The term "mucosal" means relating to any immuno-competent mucosa of the body.

The term "oromucosal" means relating to the mucosa of the buccal cavity, the sublingual mucosa and/or the mucosa of the pharynx.

The term "solid dosage form" means any solid formulation suitable for mucosal administration, such as particularly oromucosal administration, more particularly administration to mucosa of oral cavity or by sublingual administration.

The term "liquid dosage form" means any liquid formulation suitable for mucosal administration, such as particularly oromucosal administration, more particularly administration to mucosa of oral cavity or by sublingual administration.

The term "initial administration" shall in the context of the present invention mean the first ever mucosal, such as sublingual or buccal administration of a dose of an allergen composition to an individual sensitised to said allergen, or the first such administration of an allergen composition for allergen immunotherapy to an individual sensitised to said allergen after a period of at least 6 months, such as at least 6, 9 months prior to the allergen season of said allergen.

The term "seasonal allergen" means any inhalant environmental allergen originating from a biological allergen emitting source, which in at least one period each year has a level in the surroundings sufficient to elicit symptoms of allergy in at least some patients, and which in at least one period each year has a level in the surroundings insufficient to elicit symptoms of allergy in at least some patients.

The term "allergen composition" means any composition containing one or more allergens, including biological and biologically derived compositions and compositions containing synthetic allergens.

The term "up-dosing phase" means a period of treatment during which the doses of allergen composition administered are gradually increased to reach a full dose level, which is used in the following maintenance phase, and the up-dosing phase ends when the said full dose level is reached, i.e. immediately subsequent to the administration of the first full dose.

The term "maintenance phase" means a period of treatment in continuation of the up-dosing phase and during which a full dose of allergen composition is administered, the maintenance phase starting immediately subsequent to the administration of the first full dose.

The term "allergen season" means a period of time, the start of which is the first of three consecutive days, wherein the level of airborne allergen-containing particles is above a threshold value, which is 5% of the average peak value of the previous 10 years, at one or more measuring locations in the region or country, and the end of which is on the last of three consecutive days, wherein the level of airborne allergen-containing particles is below a threshold value, which is 5% of the average peak value of the previous 10 years at one or more measuring locations in the region or country.

The term "airborne allergen-containing particles" means any airborne allergen-containing particle originating from a biological allergen emitting source, including pollen from e.g. grasses, weeds, plants and trees, spores for fungi and any other biological debris from the biological allergen emitting source, which is used by the competent authorities when measuring the level of allergen in the surroundings. The expression "region or country" means the region or country, which is used by the competent authorities when monitoring the level of allergen in the surroundings. The term "peak value" means the average of the three days with the highest values of a season.

The term "SQ-u" means Standardised Quality-Unit: The SQ-u is determined in accordance with ALK-Abelló A/S's "SQ biopotency"-standardisation method, where 100,000 SQ units equal the standard subcutaneous maintenance dose. Normally 1 mg of extract contains between 100,000 and 1,000,000 SQ-Units, depending on the allergen source from which they originate and the manufacturing process used.

The precise allergen amount can be determined by means of immunoassay i.e. total major allergen content and total allergen activity.

The term "treating" means partly of wholly curing, alleviating symptoms or inhibiting causes of symptoms.

The term "preventing" means any type of prophylactic treatment.

The term "allergy" means any type of hypersensitivity reaction to an environmental allergen mediated by immunological mechanisms, including Type I-IV hypersensitivity reactions, including allergic rhinitis, asthma and atopic dermatitis.

The term "allergen" means any compound capable of eliciting allergy.

Seasonal Allergen Composition

Generally, a seasonal allergen includes any inhalant environmental allergen originating from a biological allergen emitting source, which in at least one period each year has a level in the surroundings sufficient to elicit symptoms of allergy in at least some patients, and which in at least one period each year has a level in the surroundings insufficient to elicit symptoms of allergy in at least some patients.

Thus, a seasonal allergen encompasses any seasonal, inhalant, environmental allergen originating from a biological allergen emitting source. Typically, such a seasonal allergen is an allergen derived from pollen, such as tree-, herb, weed-, and/or grass pollen allergens. Furthermore, some fungi and mould allergens occur seasonally during the year, e.g. *Alternaria* and *Cladosporium*.

Important pollen allergens from trees, grasses and herbs are such originating from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (*Cryptomeria* and *Juniperus*), Plane tree (*Platanus*), the order of Poales including i.a. grasses of the genera *Lolium, Phleum, Poa, Cynodon, Dactylis, Holcus, Phalaris, Secale*, and *Sorghum*, the orders of Asterales and Urticales including i.a. herbs of the genera *Ambrosia, Artemisia*, and *Parietaria*.

Important inhalation allergens from fungi and moulds that occur seasonally are i.a. such originating from the genera *Alternaria* and *Cladosporium*.

In a particular embodiment of the invention the allergen is Bet v 1, Aln g 1, Cor a 1 and Car b 1, Que a 1, Cry j 1, Cry j 2, Cup a 1, Cup s 1, Jun a 1, Jun a 2, Jun a 3, Ole e 1, Lig v 1, Pla l 1, Pla a 2, Amb a 1, Amb a 2, Amb t 5, Art v 1, Art v 2 Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Alt a 1, Cla h 1, Asp f 1, Mal d1, Gly m 1, Gly m 2, Gly m 3, Ara h 1, Ara h 2, Ara h 3, Ara h 4, Ara h 5 or shufflant hybrids from Molecular Breeding of any of these.

In a preferred embodiment of the invention the allergen is selected from the group consisting of a tree pollen allergen, a grass pollen allergen, a weed pollen allergen, a herb pollen allergen, a mould seasonal allergen and a fungi seasonal allergen.

In yet another embodiment of the invention the composition comprises at least two different types of allergens either originating from the same allergic source or originating from different allergenic sources, such as grass group 1 and grass group 5 allergens from different grass species, weed allergens from short and giant ragweed, fungi allergens from *Alternaria* and *Cladosporium*, and tree allergens from birch, hazel, hornbeam, oak and alder.

The allergen composition may be an allergen extract, a purified fraction of an allergen extract, a modified allergen, a recombinant allergen and a mutant of a recombinant allergen. An allergenic extract may naturally contain one or more isoforms of the same allergen, whereas a recombinant allergen typically only represents one isoform of an allergen. The mutant allergen may be a low IgE-binding mutant, e.g. a low IgE-binding allergen according to WO 99/47680, WO 02/40676 or WO 03/096869 A2. The modified allergen may be any allergen derivative modified by e.g. chemical, physical or enzymatic treatment, including e.g. allergoids. In a preferred embodiment the allergen composition is in the form of an extract. In another preferred embodiment the allergen composition is a recombinant allergen. In a further preferred embodiment the allergen composition is an allergoid. In a further preferred embodiment the allergen composition is a naturally occurring low IgE-binding mutant or a recombinant low IgE-binding mutant. Furthermore, the allergen composition may be a mixture of a number of allergens, e.g. from 2 to 10 allergens, in particular from 3 to 9 allergens, more in particular from 4 to 8, and most in particular from 5 to 7 allergens.

When the allergen composition comprises more than one allergen, the allergens may be present in equi-molar amounts or the ratio of the allergens present may vary preferably up to 1:20.

The preferred potency of a mono-dose formulation is from 100 to 1000000 SQ-u, more preferably from 500 to 500000 SQ-u, more preferably from 1000 to 300000 SQ-u, more preferably from 10000 to 200000 SQ-u, more preferably from 25000 to 150000 SQ-u and most preferable from 50000 to 100000 SQ-u.

The amount of allergen, which corresponds to a given level of potency, varies strongly depending on the allergen specie. In a further embodiment of the invention the concentration of major allergen in a mono-dose is from 0.05 to 50 μg, more preferably from 0.05 μg to 30 μg, more preferably from 0.06 μg to 25 μg, more preferably from 0.07 μg to 20 μg, more preferably from 0.08 μg to 15 μg, more preferably from 0.09 μg to 10 μg and most preferably from 0.1 μg to 7 μg.

In the field of allergy extracts, there is no international accepted standardisation method. A number of different units of extract strength i.e. bio-potency exist. The methods employed and the units used normally measure the allergen content and biological activity. Examples hereof are SQ-Units (Standardised Quality units), BAU (Biological Allergen Units), BU (biological units), UM (Units of Mass), IU (International Units) and IR (Index of Reactivity). Hence, if extracts of origins other than those disclosed herein are used, they need to be standardised against extract disclosed herein in order to determine their potency in SQ units or any of the above mentioned units. The subject matter is dealt with in "Allergenic extracts", H. Ipsen et al, chapter 20 in Allergy, principle and practise (Ed. S. Manning) 1993, Mosby-Year Book, St. Louis and Løwenstein H. (1980) Arb Paul Ehrlich Inst 75:122.

The bio-potency, i.e. the in vivo allergenic activity, of a given extract depends on a number of factors, the most important being the content of major allergens in the extract, which varies with the composition of the biological source material.

The amount of allergen extract in grams to be used for obtaining a desired bio-potency varies with the type of extract in question, and for a given type of extract the amount of allergen extract varies from one batch to another with the actual bio-potency of the extract.

For a given batch of extract, the amount of allergen extract in grams to be used for obtaining a desired bio-potency may be determined using the following procedure:

a) The bio-potency of various amounts of a reference extract is determined using one or more immunological in vivo tests to establish a relationship between bio-potency and amount of reference extract. Examples of the said immunological in vivo tests are Skin Prick Test (SPT), Conjunctival Provocation Test (CPT), Bronchial Challenge with Allergen (BCA) and various clinical trials in which one or more allergy symptoms is monitored, see for example e.g. Haugaard et al., J Allergy Clin Immunol, Vol. 91, No. 3, pp 709-722, March 1993.

b) On the basis of the established relationship between bio-potency and reference extract, the bio-potency of one or more relevant doses for use in the dosage forms of the invention is selected with due consideration to a balance of the factors of i) the effect of treating or alleviating symptoms of allergy, ii) side effects recorded in the immunological in vivo tests, and iii) the variability of i) and ii) from one individual to another. The balancing is done to obtain a maximal adequate therapeutic effect without experiencing an unacceptable level of side effect. The way of balancing the factors are well known to those skilled in the art The bio-potency of the one or more relevant doses found may be expressed in any biopotency unit available, such as SQ units, BAU, IR units, IU, cf. above.

c) From the reference extract one or more bio-potency reference standard extracts is prepared and, if used, the bio-potency unit values of the reference standard extracts are calculated on the basis of the bio-potency unit value allocated to the one or more relevant doses, e.g. such a standard for BAU can be obtained from FDA as illustrated below.

d) For the reference standard extracts of each extract type, a number of parameters for evaluating the bio-potency of extracts are selected. Examples of such evaluation parameters are total allergenic activity, the amount of defined major allergens and overall molecular composition of the extract. The total allergenic activity may be measured using an in vitro competitive immunoassay, such as ELISA and MagicLite® luminescence immunoassay (LIA), using a standardised antibody mixture raised against the extract obtained using standard methods, e.g. antibodies raised in mouse or rabbit, or a pool of allergic patients sera. The content of major allergens may e.g. be quantified by rocket immuno-electrophoresis (RIE) and compared to the reference standards. The overall molecular composition may be examined using e.g. crossed immunoelectrophoresis (CIE) and sodium dodecyl sulphate polyacrylamide gel electrophoresis (SDS-PAGE).

e) For a given batch of extract of unknown bio-potency (test extract), the amount of extract to be used for obtaining a desired bio-potency level (effective dose for use in the solid dosage form according to the present invention) may be determined as follows: For each evaluation parameter selected, the test extract is compared with the reference standard extracts using the relevant measurement methods as described above, and on the basis of the measurement results the amount of extract having the desired bio-potency is calculated.

SQ-Unit: The SQ-Unit is determined in accordance with ALK-Abelló A/S's "SQ biopotency"-standardisation method, where 100,000 SQ units equal the standard subcutaneous maintenance dose. Normally 1 mg of extract contains between 100,000 and 1,000,000 SQ-Units, depending on the allergen source from which they originate and the manufacturing process used. The precise allergen amount can be determined by means of immunoassay i.e. total major allergen content and total allergen activity.

BAU (Biological Allergen Units) is biological potency units as determined according to the requirements of the FDA for allergen product described in "Quantitative determination of relative potency of allergenic extracts" ("Methods of the allergen products testing Laboratory" "ELISA competition assay". Page 15, #49N-0012, FDA, October 1993). A dose of 100,000 SQ-Units containing grass extract equals a content of 2600-4700 BAU according to the method above. Likewise, other extracts can be assessed according to the method above.

Manner of Administration

As mentioned, according to the present invention, the allergen composition is suitable formulated for mucosal administration and is administered to the patient by mucosal administration since this route of administration is acknowledged as more safe and convenient than subcutaneous immunotherapy.

Mucosal administration may be carried out via any immuno-competent mucosa of the body. Mucosal administration includes oral, nasal, vaginal, sublingual, ocular, rectal, urinal, intramammal, pulmonal, otolar (i.e. via the ear) or buccal administration, preferably buccal or sublingual administration.

In a particular embodiment of the invention the mucosal administration is oromucosal administration, i.e. administration via buccal, sublingual and/or pharynx mucosa. Oromucosal administration comprises any administration method, wherein the formulation in part or in full comes into contact with the mucosa of the oral cavity and/or the pharynx of the patient. Oromucosal administration methods include sublingual administration and buccal administration. Thus, in a specific embodiment of the invention, the mucosal administration is sublingual administration.

Sublingual administration of allergens is a known route of administration. Administration may be carried out by placing the vaccine formulation under the tongue and allowing it to remain there for a short period of time, e.g. from 30 to 300 seconds, preferably from 45 to 240 seconds, more preferably from 60 to 180 seconds, more preferably from 90 to 150 seconds, and most preferably from 90 to 120 seconds.

Dosage Regimen

The dosage regimen used in the present invention may be any conventional dosage regimen used for mucosal allergen-specific immunotherapy in respect to selection of doses, number of doses per day, duration of treatment and frequency of administration.

However, in accordance with the mucosal allergen-specific immunotherapy of the present invention, the initial administration is performed within the allergen season of the allergen composition. In this connection the expression "initial administration" means the first ever administration of a dose of an allergy vaccine suitable for mucosal administration, such as particularly sublingual or buccal administration, containing the allergen composition or the first such administration after a period of at least nine months, such as six or three months prior to the season.

The initial administration may be given at the start of the allergen season or after the start of the season. In particular, the initial administration is given more than 1 week, more particularly more than 2 weeks, more particularly more than 3 weeks, more particularly more than 4 weeks, more particularly more than 5 weeks, more particularly more than 6 weeks, more particularly more than 10 weeks after the start of the allergen season.

The dosage regimen may be a mono-dose regimen, wherein only one dose of allergen composition is used throughout the entire treatment period. Alternatively, the dosage regimen may comprise an up-dosing phase followed by a maintenance phase. However, in an advantageous embodiment of this invention, the dosing regimen comprises no up-dosing phase, i.e. the initial administration is performed without up-dosing phase.

In one embodiment of the invention, the subject is subjected to a dosage regimen comprising one or two (twice) daily administrations of the dosage form. In another embodiment of the invention the dosage regimen comprises administration of the vaccine every second day, every third day or every fourth day. For instance, the dosage regimen comprises administration of the vaccine for a period of more than 4 weeks, preferably more than 8 weeks, more preferably more than 12 weeks, more preferably more than 16 weeks, more preferably more than 20 weeks, more preferably more than 24 weeks, more preferably more than 30 and most preferably more than 36 weeks. In a particular embodiment of the invention the dosage regimen comprises administration of the vaccine for at least the duration of the allergen season. In a particular embodiment of the invention, the duration of the dosage regimen is from 12 months to 48 months, preferably from 24 months to 42 months, more preferably from 30 months to 40 months, and most preferably from 34 months to 38 months.

The period of administration of the dosage regimen may a continuous period. Alternatively, the period of administration is a discontinuous period interrupted by one or more periods of non-administration. Preferably, the (total) period of non-administration is shorter than the (total) period of administration. In a preferred embodiment of the invention, the dosage regimen comprises administration in the allergy season of at least three consecutive years.

Dosage Form

As mentioned, the dosage form for use in the present invention is preferably a solid dosage form, such as any solid dosage form suitable for administration to a mucosal tissue, such as by buccal or sublingual administration, including compressed tablets, non-compressed tablets, coated tablets, non-coated tablets, powders, gels, suppositories, capsules and pastes.

An example of a non-compressed solid dosage form is lyophilized, fast-dissolving solid dosage forms, such as dosage forms marketed under the name of Zydis® and dosage forms disclosed in WO 04/047794. Such dosage forms may e.g. be manufactured by preparing a solution of matrix-forming agents and the active substance, filling the solution into the depressions of a multilayer laminated blister sheet, and subjecting the loaded sheet to freezing and freeze drying. Non-compressed, fast-dissolved dosage forms are particularly suitable for oromucosal administration.

Alternatively, mucosal administration may be performed with a liquid dosage form, such as droplets or sprays. In particularly, the liquid dosage form is one suitable for being administered oromucosally, such as specifically to the oral mucosa, such as sublingually.

The dosage form of the invention may further comprise any adjuvant and other excipients suitable for a solid or liquid dosage form. Such excipients are well-known to the person skilled in the art and include i.e. wetting agents, plasticizers, colouring substances, fillers, preservatives, viscosity adjusting agents, buffering agents, pH adjusting agents, isotonicity adjusting agents, mucoadhesive substances, and the like. Examples of formulation strategies are well-known to the person skilled in the art.

The adjuvant may be any adjuvant suitable for a solid dosage form for mucosal administration, including oxygen-containing metal salts, e.g. aluminium hydroxide, heat-labile enterotoxin (LT), cholera toxin (CT), cholera toxin B subunit (CTB), polymerised liposomes, mutant toxins, e.g. LTK63 and LTR72, microcapsules, interleukins (e.g. IL-1β, IL-2, IL-7, IL-12, INFγ), GM-CSF, MDF derivatives, CpG oligonucleotides, LPS, MPL, phosphophazenes, Adju-Phos®, glucan, antigen formulation, liposomes, DDE, DHEA, DMPC, DMPG, DOC/Alum Complex, Freund's incomplete adjuvant, ISCOMs®, LT Oral Adjuvant, muramyl dipeptide, monophosphoryl lipid A, muramyl tripeptide, and phospatidylethanolamine.

Aqueous solutions of oxygen-containing metal salts typically have the form of gels. It is possible to convert an aqueous solution of an oxygen-containing metal salt to a solid form, e.g. by lyophilisation, which is re-wetted and re-solubilised upon administration to a subject. When subjecting oxygen-containing metal salts to lyohilisation, it is common practise to use a protective agent, such as a saccharide, a sugar-alcohol and/or an amino acid, e.g. a described in WO 2007/038926.

In a particular embodiment of the invention, the dosage form of the invention comprises an oxygen-containing metal salt adjuvant. Preferably, the metal cation of the oxygen-containing metal salt is selected from the group consisting of Al, K, Ca, Mg, Zn, Ba, Na, Li, B, Be, Fe, Si, Co, Cu, Ni, Ag, Au and Cr.

The anion of the oxygen-containing compound may be any oxygen-containing anion, including an organic or inorganic anion, or a combination of organic and inorganic anions. Examples of suitable oxygen-containing metal salts are e.g. those, wherein the anion is selected from the group consisting of sulphates, hydroxides, phosphates, nitrates, iodates, bromates, carbonates, hydrates, acetates, citrates, oxalates, and tartrates, as well as mixed forms thereof. The oxygen-containing metal salts further comprise coordination complexes. A definition of coordination complexes is given in e.g. The Handbook of Chemistry and Physics 56 Ed., Section B, Chapter 7 (197576).

Within the present context, the expression "mixed forms" is intended to include combinations of the various anions as well as combinations with e.g. chlorides, and sulphides.

Examples of oxygen-containing metal salts according to the invention are aluminium hydroxide, aluminium phosphate, aluminium sulphate, aluminium acetate, potassium aluminium sulphate, calcium phosphate, calcium tartrate, Maalox (mixture of aluminium hydroxide and magnesium hydroxide), beryllium hydroxide, zinc hydroxide, zinc carbonate, zinc sulphate, and barium sulphate.

Most preferred are aluminium hydroxide, aluminium phosphate, aluminium acetate, calcium phosphate, calcium tartrate and zinc sulphate.

The pI of the oxygen-containing metal salt is typically in the range of 2-11. The pI for allergen proteins is typically in the range of 4-9. Preferably, the allergen and oxygen-containing metal salt are selected so that the pI of the allergen is lower than the pI of the oxygen-containing metal salt.

When using e.g. aluminium hydroxide as oxygen-containing metal salt, the concentration of aluminium hydroxide in the solution used for lyophilisation is preferably 0.035-1000 mg/ml, more preferably 0.10-100 mg/ml, more preferably 0.25-10 mg/ml, and most preferably 0.5-5 mg/ml. For the other oxygen-containing metal salts, the concentration of the metal salt is preferably 0.035-1000 mg/ml, more preferably 0.35-100 mg/ml, more preferably 0.7-50 mg/ml, and most preferably 1.0-20 mg/ml. The concentration of allergen in the solution is preferably 0.01-100 mg/ml, more preferably 0.1-

10 mg/ml. The ratio of oxygen-containing metal salt to allergen is preferably from 0.1 to 100, more preferably from 1 to 20. The degree of allergen adsorbed to the oxygen-containing metal salt is typically from 5 to 99%, more preferably from 10 to 99% of the added amount. The adsorption of allergen to the oxygen-containing metal salt depends on the buffer system and the reaction conditions, including temperature and reaction time, under which the adsorption takes place.

Oxygen-containing metal salts can be characterised by a variety of physical-chemical parameters like adsorption, solubility and dissolution properties, ionic charge measured as the isoelectric point pI (pH where the net charge of the substance is zero for a dissociationable compound), dissociation constants, complex coordination, electronic configurations, valence, bonding orbitals and antibonding orbitals, depot properties, adhesion properties, surface characteristics, particle characteristics, and adjuvanticity.

It is believed that the biologically active substance is adsorbed (or coupled) to the oxygen-containing metal salt, and this adsorption contributes to the efficacy of the vaccine. Several factors may be important or influence the adsorption between the active substance and the oxygen-containing metal salt (see e.g. P. M. Callahan et al., Pharmaceutical Research Vol. 8, No. 7, 851-858 (1991), and Vaccine Design. The Subunit and Adjuvant Approach). These factors include pH, the length of time the adsorption reaction is carried out for, mixing conditions, concentrations of the various components in the vaccines, containers, temperature, storage, buffer and excipients. It has further been found that the adsorption of the active substance may be influenced by the net/overall charge of the metal salt and the charge of the active substance, both of which are pH dependent. A further feature believed to be of importance is the solubility of the oxygen-containing metal salts.

Another feature of oxygen-containing salts is the protection of the active substance either by maintaining the ideal pH for the active substance in the microenvironment, thus preventing acid degradation, or by protecting the active substance against enzymatic degradation thereby allowing the substance to be delivered.

Furthermore, some of the oxygen-containing metal salts have a buffer capacity. This may result in an in vivo microenvironment within the vaccine formulation, which protects the active substance from the degradable environment.

A further feature of the oxygen-containing metal salt(s) is their capability to adhere to the mucosal membrane. This is believed to increase absorption of the allergen through the mucosal membrane.

For several of the oxygen-containing metal salts (e. g. $Al(OH)_3$, $AlPO_4$, $Ca_3PO_4$) the particle size range is between 0.5 and 15 μm.

EXAMPLES

Example 1

Safety Assessment of Intra-Seasonal Start of Allergen-Specific Immunotherapy with Sublingual Allergy Vaccine Study Design This study is based on data relating to intra-seasonal start of treatment in patients with pollen allergy. The data include patient data, allergy history of patients, clinical results with treatment using a vaccine for treating grass pollen allergy, administration protocols and recorded allergic reactions during the period of treatment. Data for 141 patients, who had the initial administration of TEST PRODUCT® within the grass pollen season, was obtained. For 126 patients a follow-up visit was documented.

The start of the pollen season was determined according to pollen data from Stiftung Deutscher Polleninformationsdienst defining the start of the season as the first of three consecutive days with a pollen count $\geq 6/m^3$. Patients were eligible for inclusion in the study when the initial administration of Trial Product® took place between Apr. 10, 2007 and Aug. 31, 2007 and the treatment commenced immediately after this test administration. GRAXAZ® was administered to patients once daily.

Trial Product

A rapidly dissolving oral lyophilisate tablet for sublingual administration containing an extract of grass pollen allergens (*Phleum Pratense*) was used as trial product. Dosage was 75,000 SQ-T. Trial Product was obtained from ALK-Abelló A/S and known under the trade name GRAXAZ®.

Statistical Methods

A descriptive statistical analysis was performed. The evaluation according to the principle of matched pairs used a study with a pre-seasonal start of treatment with Trial Product® as reference. The matched pairs were constructed using three criteria:

Age (Years) ≤17, 18-50, >50)
Clinical manifestation (rhinitis or rhinoconjunctivitis (no bronchial complaints), bronchial asthma (with or without rhinitis or rhinoconjunctivitis))
Treatment duration (first intake only, at least one subsequent visit).

Patients

Treatment with Trial Product® was initiated in the season for N=141 documented patients. For each of these patients a partner with the same characteristics was randomly identified in the population of the study with a pre-seasonal start of Trial Product® treatment. For the patients in the study with a pre-seasonal start, the duration of the pre-seasonal treatment was at least 10 days.

The age of patients ranged from 9 to 68 years (median: 32 years). The median duration of complaints was 6 years since first occurrence of allergic symptoms. A grass pollen allergy had been diagnosed for a period of at least 2 years. The gender was nearly balanced. In the majority of patients the complaints were manifested as rhinitis (97.2%) and as conjunctivitis (72.3%). Bronchial asthma was registered in 31.2% of the patients. One or more concomitant Type I allergies were present in 48.2%, predominantly other pollen allergies (39.7%), animal epithelia allergies (16.3%) and house dust mites allergies (15.6%). An oral allergy syndrome was documented for 9 patients (6.5%).

The status of immunotherapy was classified as follows:
First-time immunotherapy of the grass pollen allergy: 78.0%
New immunotherapy after previous complete immunotherapy: 13.5%
Change-over to Trial Product® from incomplete immunotherapy: 8.5%.
In 5 further patients a previous treatment was reported:
Dust mites allergies (3 patients)
Tree mix (2 patients)
Immunotherapy for a concomitant allergy was registered for 24 patients.

In this Example the terms "pre-seasonally" and "intra-seasonally" mean before and in, respectively, the pollen season of the specific allergen, to which the patients were allergic and with which the patients were treated.

Results on Adverse Drug Reactions (ADR)
Intra-Seasonal Start of Treatment

In total 46 patients experienced Adverse Drug Reactions (ADR) after the initial administration. The ADR was tolerable for 45 patients and intolerable for 1 patient, for which Trial Product was not prescribed. Symptom-relieving drugs like oral antihistamines were administered to 17 patients (12.1%) prior to the start of the administration of Trial Product (pre-medication). The incidence of ADR for patients receiving no pre-medication was 32/89 (36.0%). The incidence of ADR for patients receiving pre-medication was 5/17 (29.4%). There was no statistically significant difference between the two groups ($X^2$ test: p=0.6040).

Trial Product was prescribed in 136 cases (96.5%). 10 patients did not return for a subsequent visit, which were reported for 126 patients. Among the 5 patients who discontinued the treatment after the initial test administration, only one patient stopped due to an intolerable reaction. For the patients receiving Trial Product, symptom-relieving medication was recommended for 21 patients, but information about whether symptom-relieving medication was recommended was not available for all patients. The median number of intra-seasonal treatment days was 87.5. ADR occurring within season were observed in nine patients. The ADR are classified as follows (15 events on Systemic Organ Class (SOC) level):

Gastrointestinal disorders, including symptoms in the oral cavity and throat: N=9 (7.1%)
General disorders and administration site conditions: N=1 (0.8%)
Respiratory, thoracic and mediastinal disorders: N=4 (3.2%)
Skin and subcutaneous tissue disorders: N=1 (0.8%).

Pre-Seasonal Start of Treatment

For all patients of the population subjected to intra-seasonal start of treatment, a partner could be identified in the population subjected to pre-seasonal start of treatment (reference study). After the initial administration, in total 53 patients experienced tolerable (52) or intolerable (1) Adverse Drug Reactions in the reference study. In the reference study, Trial Product was prescribed to all patients, but according to the third criterion of matched pairs, exactly 126 returned to a subsequent visit. In the patient group of the reference study, ADR were observed in 26 cases. These reactions are classified as follows (40 events on SOC level)

Eye disorders: N=3 (2.4%)
Gastrointestinal disorders, including symptoms in the oral cavity and throat: N=18 (14.3%)
General disorders and administration site conditions: N=3 (2.4%)
Immune system disorders: N=1 (0.8%)
Injury, poisoning and procedural complications: N=1 (0.8%)
Investigations: N=1 (0.8%)
Nervous system disorders: N=2 (1.6%)
Respiratory, thoracic and mediastinal disorders: N=7 (5.6%)
Skin and subcutaneous tissue disorders: N=4 (3.2%).

Matched Pairs for the Analysis of Initial Administration of Trial Product

The intra-pair comparison of the population subjected to intra-seasonally start of treatment and the reference study population after the initial administration is given in Table 1.

TABLE 1

Matched pairs analysis of the intra-seasonal treatment population and the reference group population after initial administration of Trial Product (Bowker test: p = 0.8352)

| Intra-seasonal study | Pre-seasonal study | | |
|---|---|---|---|
| | No ADR | Tolerable ADR | Intolerable ADR |
| No ADR | 62 | 32 | 1 |
| Tolerable ADR | 25 | 20 | — |
| Intolerable ADR | 1 | — | — |

As will appear from Table 1, for 62 patient pairs both partners had no ADR, and for 20 patient-pairs both partners had tolerable ADR. 25 patients of the intra-seasonal study had tolerable ADR, whereas their partners from the pre-seasonal study had no ADR, and 32 patients from the intra-seasonal study had no ADR, whereas their partners from the pre-seasonal study had tolerable ADR. Finally, 1 patient of the intra-seasonal study had intolerable ADR, whereas the partner from the pre-seasonal study had no ADR, and 1 patient from the intra-seasonal study had no ADR, whereas the partner from the pre-seasonal study had intolerable ADR.

The Bowker test shows no relevant differences between the two treatment populations. In total 59 pairs yielded discordant values, the relation 26:33 in favour of intra-seasonal initiation of Trial Product therapy is not relevant.

Conclusion

Treatment with Trial Product in a dosage regimen using intra-seasonal start of administration is well-tolerated, as 45 patients of 141 patients experienced tolerable ADR after the initial administration, whereas only one patient experienced intolerable ADR. Furthermore, only 9 patients of 126 patients experienced tolerable ADR in the allergen season after continued treatment and no patient experienced intolerable ADR in the season. In comparison, with pre-seasonal start of treatment 52 patients of 141 patients experienced tolerable ADR after initial administration Also, there is no indication that Trial Product is less well-tolerated, when treatment is started intra-seasonally as compared to when treatment is started pre-seasonally.

Example 2

Pharmacodynamic effect and tolerability of treatment initiated in the grass pollen season in subjects with seasonal grass pollen induced rhinoconjunctivitis.

Trial Objective

To investigate the tolerability as well as the pharmacodynamic effect of Trial Product (natural allergen extract of grass pollen) compared to placebo when treatment of patients allergic to grass pollen is initiated during the grass pollen season.

Trial Product

A rapidly dissolving oral lyophilisate tablet for sublingual administration containing an extract of grass pollen allergens (*Phleum Pratense*) was used as trial product. Dosage was 75,000 SQ-T. Trial Product was obtained from ALK-Abelló A/S and known under the trade name GRAXAZ®.

Trial Design

The present trial was a randomised, parallel-group, double-blind, placebo-controlled, multi-centre trial where subjects received either Trial Product or placebo once daily starting during the grass pollen season. The subjects were treated throughout the grass pollen season for at least 8 weeks (+1-2 weeks).

Subjects

Subjects consisted of adults with grass pollen induced rhinoconjunctivitis with or without controlled or partly controlled asthma with clinically relevant symptoms, a positive skin prick test (SPT) response to *phleum pratense*, and diagnosed with specific IgE test to grass pollen. The subjects may not have been in treatment with immunotherapy with grass pollen allergens within the previously five years. A total number of 276 subjects were included.

Allergen Exposure

Grass pollen counts were collected by regional agencies and accordingly they reflected the grass pollen counts present in the area of the centre. It was anticipated that most subjects in the trial resided and/or work in the general geographic vicinity of the investigator's office and therefore were exposed to the seasonal grass pollen levels measured and recorded. The beginning of the grass pollen season was defined as the first of three consecutive days with grass pollen counts of $\geq 10$ grains/m$^3$ (corresponding to at least moderate pollen forecast by Deutscher Wetterdienst).

Pharmacodynamic/Immunological Assessments

Efficacy was evaluated primarily by demonstrating a difference in the level of IgE-blocking antibodies approximately 8 weeks after treatment initiation in subjects treated with Trial Product compared to subjects treated with placebo. Secondarily, the efficacy was evaluated by determining levels of IgE and IgG$_4$ antibodies approximately 8 weeks after treatment initiation in subjects treated with Trial Product compared to subjects treated with placebo. The primary pharmacodynamic effect endpoint was selected to demonstrate the initiation of an immunomodulatory effect of Trial Product when treatment is initiated within the grass pollen season.

Tolerability Assessment

Tolerability was evaluated by total number of Adverse Events (AE), type and severity during the trial period, the total number of discontinuations, the rhinoconjunctivitis symptoms, use of allergy and/or asthma medication, FEV1, vital signs and physical examination approximately 8 weeks after treatment initiation. Tolerability is a main aspect of in-season initiation of allergen-specific immunotherapy and was monitored by the investigator and subject throughout the treatment part of the trial.

The maximum severity of an AE was assessed by the investigator using the following definitions:

Mild: Transient symptoms, no interference with the subject's daily activities.

Moderate: Marked symptoms, moderate interference with the subject's daily activities.

Severe: Considerable interference with the subject's daily activities, unacceptable.

Results

Pharmacodynamic Effect

The level of IgE-blocking factor increased in both treatment groups during the treatment period with a significantly greater increase in the Trial Product group.

Concerning, the secondary pharmacodynamic endpoints, the level of IgE increased considerably more during the treatment period in the Trial Product group compared with placebo. Non-parametric analysis of the change from baseline in IgE showed that this difference was significantly in favour of Trial Product. The level of IgG$_4$ increased considerably more during the treatment period in the Trial Product group compared with placebo. Non-parametric analysis of the change from baseline in IgG$_4$ showed that this difference was significantly in favour of Trial Product Tolerability A total of 39% of the subjects experienced at least 1 AE related to the treatment; 44% in the Trial Product group and 18% in the placebo group. The majority of the treatment-related AEs were mild (72%) or moderate (28%) in severity. None of the AEs were considered as serious. The most frequently reported AEs related to Trial Product treatment were mostly local reactions in ear, mouth and throat (oral pruritus in 18% of the subjects), throat irritation (7%), ear pruritus (4%), and cough (4%).

The tolerability results could be summarized as follow:

In-season initiation of Grazax treatment was generally well tolerated.

The majority of the AEs (including AEs related to Grazax) were mild or moderate in severity.

The most frequently reported AEs related to Grazax treatment were local reactions in ear, mouth and throat with oral pruritus being the most frequent.

24 subjects experienced at least 1 of the 3 pre-defined SMQs (anaphylactic reaction, angiodema and asthma/bronchospasm). Most of these subjects were in the Grazax group. 4 subjects experienced AEs classified within the SMQ anaphylactic reaction, all belonging to the Grazax group. These reactions were all mild or moderate in severity, all subjects stayed in the trial, and all subjects fully recovered.

No obvious difference was observed between the Grazax and placebo group with regard to the rhinoconjunctivitis symptom score although the score was slightly lower in the Grazax group both during the whole treatment period and during the GPS.

No obvious difference was observed between the Grazax and placebo group with regard to the use of allergy/asthma medication although the number of subjects using medication and the mean number of days with medication were slightly lower in the Grazax group compared to placebo No safety concerns were observed for FEV1, vital signs and physical examination.

Conclusion

The present trial demonstrates that in-season initiation of Trial Product induces an immunomodulatory response after approximately 9 weeks of treatment. In addition, the overall tolerability profile for Trial Product treatment initiated during the grass pollen season was comparable to what has previously been observed in other Trial Product trials in which treatment was initiated prior to the season.

In the analyses of the phamacodynamic effect parameters IgE-blocking factor, IgE, and IgG$_4$, a significant immunological response in subjects treated with Trial Product was revealed with significantly higher inductions of IgE-blocking factor, IgE, and IgG$_4$ observed for the Trial Product group as compared with the placebo group after approximately 9 weeks of treatment. These results are in accordance with immunological results obtained in other clinical trials performed with Trial Product.

In-season initiation of Trial Product was generally well tolerated and the tolerability was comparable to what has been observed in other clinical trials performed with Trial Product in which treatment was initiated prior to the grass pollen season.

The most frequently reported IMP related adverse events were mild to moderate local reactions in the mouth, throat, or ear—primarily oral pruritus. No serious adverse events related to Trial Product were reported during the trial. No obvious difference between Trial Product and placebo was observed with regard to rhinoconjunctivitis symptoms or the use of rhinoconjunctivitis and/or asthma medication further supporting the acceptable tolerability of in-season initiation of Trial Product treatment. Finally, no safety concerns were observed concerning $FEV_1$, vital sign or physical examinations.

The invention claimed is:

1. A method for allergen specific immunotherapy for treating allergy to a seasonal allergen in an allergic patient, comprising sublingual administration of a solid dosage form of an allergen extract comprising said seasonal allergen, wherein said administration is in a mono-dose dosage regimen, and initial administration is performed within the allergen season of the seasonal allergen.

2. The method according to claim 1, wherein the initial administration is given more than 1 week after the start of the allergen season.

3. The method according to claim 1, wherein the dosage form is administered daily.

4. The method according to claim 1, wherein the duration of the dosage regimen is from 12 months to 48 months.

5. The method according to claim 1, wherein said seasonal allergen is selected from the group consisting of a tree pollen allergen, a grass pollen allergen, a weed pollen allergen, a herb pollen allergen, a seasonal mould allergen and a fungi seasonal allergen.

6. The method according to claim 1, wherein the solid dosage form is selected from the group consisting of compressed tablets, non-compressed tablets, coated tablets, non-coated tablets, powders, gels, suppositories, capsules and pastes.

7. The method according to claim 1, wherein the solid dosage form is a compressed tablet or a non-compressed tablet.

8. The method according to claim 7, wherein the non-compressed tablet is a lyophilized, fast dissolving tablet.

9. A method for allergen specific immunotherapy for treating allergy to a grass pollen allergen in an allergic patient, comprising sublingual administration of a solid dosage form of an allergen extract comprising said grass pollen allergen, wherein said administration is in a mono-dose dosage regimen, and initial administration is performed within the allergen season of the grass pollen allergen.

10. The method according to claim 9, wherein the grass pollen allergen is of a genus selected from the group consisting of *Lolium, Phleum, Poa, Cynodon, Dactylis, Holcus, Phalaris, Secale* and *Sorghum*.

11. The method according to claim 10, wherein the grass pollen allergen is of the genus *Phleum*.

12. The method according to claim 9, wherein the solid dosage form is a compressed tablet or a non-compressed tablet.

13. The method according to claim 12, wherein the non-compressed tablet is a lyophilized, fast dissolving tablet.

14. The method according to claim 9, wherein the dosage form is administered daily.

15. The method according to claim 9, wherein the duration of the dosage regimen is from 12 months to 48 months.

16. The method according to claim 1, wherein the mono-dose dosage regimen comprises no up-dosing phase.

17. The method according to claim 9, wherein the mono-dose dosage regimen comprises no up-dosing phase.

18. The method according to claim 2, wherein said initial administration is given more than 2 weeks after the start of the allergen season.

19. A method for allergen specific immunotherapy for treating allergy to a weed pollen allergen in an allergic patient, comprising sublingual administration of a solid dosage form of an allergen extract comprising said weed pollen allergen, wherein said administration is in a mono-dose dosage regimen, and initial administration is performed within the allergen season of the weed pollen allergen.

20. The method according to claim 19, wherein the weed pollen allergen is of the genus *Ambrosia*.

21. The method according to claim 19, wherein the solid dosage form is a compressed tablet or a non-compressed tablet.

22. The method according to claim 21, wherein the non-compressed tablet is a lyophilized, fast dissolving tablet.

23. The method according to claim 19, wherein the dosage form is administered daily.

24. The method according to claim 19, wherein the duration of the dosage regimen is from 12 months to 48 months.

25. The method according to claim 19, wherein the mono-dose dosage regimen comprises no up-dosing phase.

* * * * *